(12) United States Patent
Greenberg et al.

(10) Patent No.: US 8,968,389 B2
(45) Date of Patent: Mar. 3, 2015

(54) ENDOLUMINAL PROSTHESIS WITH A VALVE ARRANGEMENT

(71) Applicant: Cleveland Clinic Foundation, Cleveland, OH (US)

(72) Inventors: Roy K. Greenberg, Bratenahl, OH (US); Karl J. West, Geneva, OH (US); Stephen Benefit, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/722,169

(22) Filed: Dec. 20, 2012

(65) Prior Publication Data

US 2013/0172984 A1    Jul. 4, 2013

Related U.S. Application Data

(60) Provisional application No. 61/580,986, filed on Dec. 28, 2011.

(51) Int. Cl.
| | |
|---|---|
| *A61F 2/06* | (2013.01) |
| *A61F 2/82* | (2013.01) |
| *A61F 2/954* | (2013.01) |
| *A61F 2/07* | (2013.01) |
| A61F 2/89 | (2013.01) |

(52) U.S. Cl.
CPC . *A61F 2/82* (2013.01); *A61F 2/954* (2013.01); *A61F 2/07* (2013.01); *A61F 2002/061* (2013.01); *A61F 2002/067* (2013.01); *A61F 2/89* (2013.01); *A61F 2002/075* (2013.01); *A61F 2220/0075* (2013.01)
USPC ................ 623/1.24; 623/1.28; 623/23.68

(58) Field of Classification Search
USPC ............ 623/1.24, 1.28, 2.1, 2.12, 2.13, 23.68
See application file for complete search history.

(56) References Cited

U.S. PATENT DOCUMENTS

| | | | |
|---|---|---|---|
| 4,728,328 A | 3/1988 | Hughes et al. | |
| 5,522,881 A | 6/1996 | Lentz | |
| 5,755,772 A | 5/1998 | Evans et al. | |
| 5,807,349 A * | 9/1998 | Person et al. ................. | 604/247 |
| 6,126,686 A * | 10/2000 | Badylak et al. .............. | 623/1.24 |
| 6,287,335 B1 | 9/2001 | Drasler et al. | |

(Continued)

FOREIGN PATENT DOCUMENTS

| | | |
|---|---|---|
| WO | 2006/028925 | 3/2006 |
| WO | 2008/057569 | 5/2008 |

OTHER PUBLICATIONS

Extended European Search Report and Written Opinion, dated May 28, 2014, corresponding application No. EP 12275213, filed Dec. 20, 2012, search completed Jan. 20, 2014.

*Primary Examiner* — Randy Shay
*Assistant Examiner* — Dinah Baria
(74) *Attorney, Agent, or Firm* — Brinks Gilson & Lione

(57) ABSTRACT

The present embodiments provide a stent graft having a tubular configuration defining a lumen therethrough, the stent graft having a proximal section and a distal section. A folded section is positioned between the proximal section and the distal section. The folded section includes a first fold directed toward the distal end and engaged with the proximal section and a second fold directed toward the proximal end and engaged with the distal section. A valve arrangement is positioned in at least one of the first and second folds providing access from an exterior of the graft to the interior of the stent graft for insertion of an additional device.

19 Claims, 9 Drawing Sheets

(56) References Cited

U.S. PATENT DOCUMENTS

| | | |
|---|---|---|
| 6,451,051 B2 | 9/2002 | Drasler et al. |
| 6,645,242 B1 | 11/2003 | Quinn |
| 6,773,456 B1 | 8/2004 | Gordon et al. |
| 6,945,942 B2 * | 9/2005 | Van Bladel et al. ............ 600/567 |
| 7,510,571 B2 | 3/2009 | Spiridigliozzi et al. |
| 7,678,141 B2 | 3/2010 | Greenan et al. |
| 7,766,959 B2 | 8/2010 | DiMatteo et al. |
| 2003/0199967 A1 | 10/2003 | Hartley et al. |
| 2006/0085060 A1 | 4/2006 | Campbell |
| 2007/0250154 A1 | 10/2007 | Greenberg et al. |
| 2008/0097578 A1 | 4/2008 | Erickson et al. |
| 2008/0114446 A1 | 5/2008 | Hartley et al. |
| 2008/0147163 A1 * | 6/2008 | Allen ........................... 623/1.14 |
| 2011/0087318 A1 | 4/2011 | Daugherty et al. |

* cited by examiner

ENDOLUMINAL PROSTHESIS WITH A VALVE ARRANGEMENT

RELATED APPLICATIONS

The present application claims priority to U.S. Provisional Patent Application Ser. No. 61/580,986 filed Dec. 28, 2011, the entirety of which is hereby incorporated by reference.

BACKGROUND

This invention relates generally to an endoluminal prosthesis and particularly to a endoluminal prosthesis having a valve arrangement that is implantable within the human or animal body for the repair of damaged vessels, ducts or other physiological passageways and cavities, and systems and methods for facilitating deployment of such an endoluminal prosthesis.

The physiological passageways and cavities of human and animal bodies, for example, blood vessels and ducts, occasionally weaken or even rupture. One common surgical intervention for weakened, aneurysmal or ruptured passageways or ducts involves the use of an endoluminal prosthesis to provide some or all of the functionality of the original, healthy passageway or duct and/or to preserve any remaining vascular integrity by replacing a length of the existing passageway or duct wall that spans the site of failure or defect. Endoluminal prostheses may be of a unitary construction or may be comprised of multiple prosthetic modules.

A modular prosthesis allows a surgeon to accommodate a wide variation in vessel morphology while reducing the necessary inventory of differently sized prostheses. For example, aortas vary in length, diameter and angle between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system may also accommodate additional deployment options by allowing the proper placement of one module before the implantation of an adjoining module.

Generally, when deploying an endovascular prosthesis into a body lumen, it may be possible to obtain access to the body lumen from each end of the lumen, thereby facilitating placement of a device in the lumen. There can be problems, however, if the aneurysm of the aorta extends down into one or the other of the iliac arteries. Each of the common iliac arteries branches into the internal and external iliac arteries and it is necessary in such a situation that a blood flow path can be directed through an endovascular stent graft into each of these arteries. The internal iliac artery which extends from the common iliac artery below the aortic bifurcation is for all intents and purposes a blind vessel because there is no practical way of performing an endovascular minimally invasive procedure into that vessel other than by entry from the common iliac artery.

BRIEF SUMMARY

The present embodiments provide a stent graft having a tubular configuration defining a lumen therethrough, the stent graft having a proximal section and a distal section. A folded section is positioned between the proximal section and the distal section. The folded section includes a first fold directed toward the distal end and engaged with the proximal section and a second fold directed toward the proximal end and engaged with the distal section. A valve arrangement is positioned in at least one of the first and second folds.

In one aspect, the folded section of the endoluminal prosthesis further includes an inner wall, a central wall, and an outer wall formed from the first and second folds. In another aspect, the valve arrangement of the endoluminal prosthesis comprises a slit valve. In another example, the valve arrangement is disposed through the second fold of the folded section. The valve arrangement provides access to the lumen of the prosthesis, while also preventing the possibility of leaks into the prosthesis.

In another aspect, an endoluminal prosthesis assembly includes a stent graft having a main graft body having a tubular configuration defining a lumen therethrough. At least one leg section is attached distal to the main graft body and having a lumen in fluid communication with the main lumen. The leg section includes a proximal section and a distal section. A folded section is positioned between the proximal section and the distal section of the leg section, the folded section having a first fold directed toward the distal end and engaged with the proximal section and a second fold directed toward the proximal end and engaged with the distal section. A valve arrangement is positioned in at least one of the first and second folds. In one embodiment, the valve arrangement is disposed through the second end of the folded section at a proximal fold line. In another embodiment, the second fold of the folded section is partially disposed with the lumen of the graft. In another embodiment, the valve arrangement is positioned between two adjacent apices of a stent attached to an exterior surface of the graft.

In yet another aspect, an endoluminal prosthesis includes a graft having a tubular configuration defining a lumen therethrough, the graft having a proximal section and a distal section. A plurality of stents is attached about an outer surface of the graft, the stents having a generally undulating configuration. A slit valve arrangement is disposed through an outer surface of the graft. In some aspects, the slit valve arrangement has an open diameter of about 4 mm.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

DETAILED DESCRIPTION OF THE DRAWINGS AND THE PRESENTLY PREFERRED EMBODIMENTS

Figure 1:
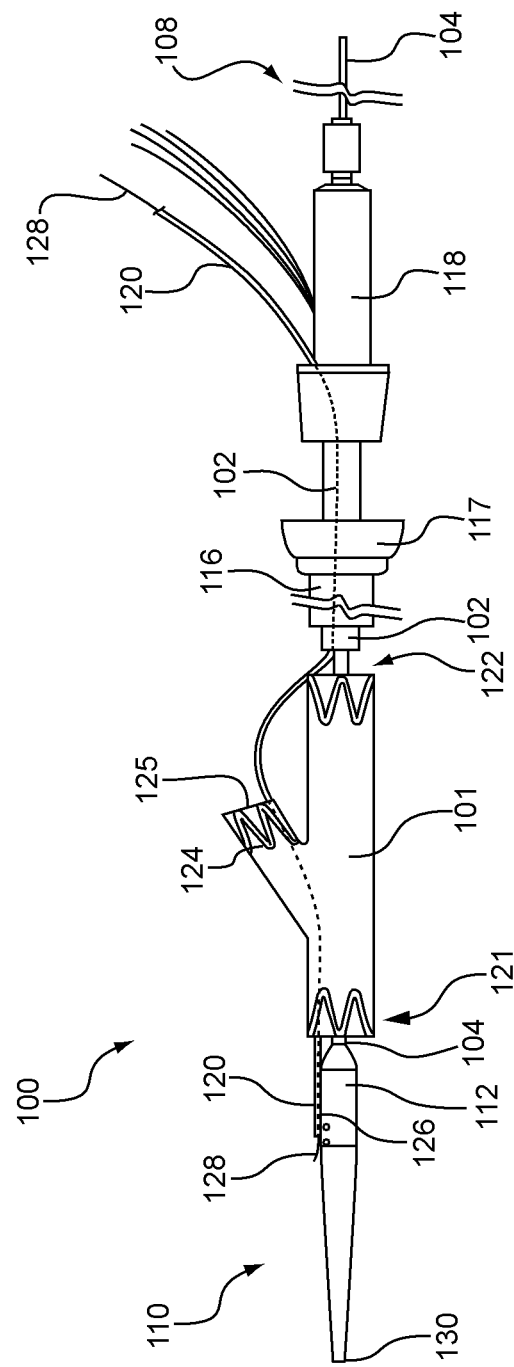
FIG. 1 shows a schematic view of a deployment device for an embodiment of an endoluminal prosthesis.

Unless defined otherwise, all technical and scientific terms used herein have the same meaning as commonly understood by one of ordinary skill in the art to which this invention pertains.

The term "prosthesis" means any device for insertion or implantation into, or replacement, for a body part or function of that body part. It may also mean a device that enhances or adds functionality to a physiological system. The term prosthesis may include, for example and without limitation, a stent, stent-graft, filter, valve, balloon, embolization coil, and the like.

The term "endoluminal" refers to or describes the internal or inside of a lumen, duct, and other passageways or cavities located in a human or other animal body. A lumen or a body passageway may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include, without limitation, blood vessels, respiratory ducts, gastrointestinal ducts, such as the biliary duct, intestines, the esophagus, the pericardial cavity, the thoracic cavity, the pericardial cavity, and the like. Accordingly, the terms "endoluminal device" or "endoluminal prosthesis" describe devices that can be placed inside or moved through any such lumen or duct.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may constitute an endoluminal prosthesis. The graft may be comprised of a single material, a blend of materials, a weave, a laminate, or a composite of two or more materials. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, sutures or the like.

The terms "patient," "subject," and "recipient" as used in this application may refer to any animal, particularly humans.

The terms "proximal" and "distal" will be used to describe opposing axial ends of the delivery system, as well as the axial ends of various component features. The term "proximal" is used to refer to the end of the system (or component thereof) that is initially inserted into the patient, or that is closest to the patient during use. The term "distal" is used to refer to the end of the system (or component thereof) that is closest to the operator during use of the system.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Figure 2:
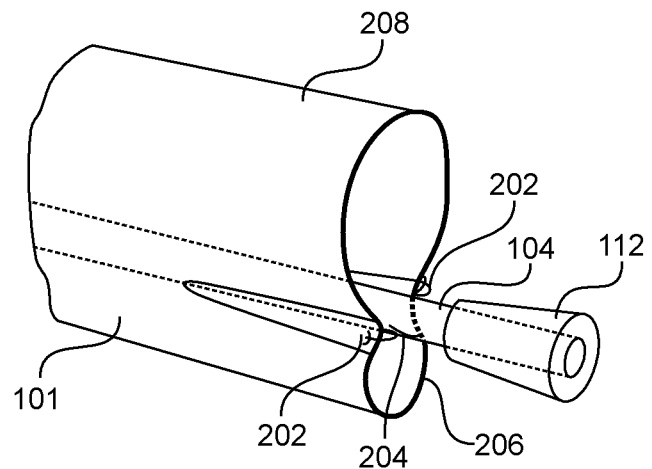
FIG. 2 shows a retention apparatus for retaining the proximal end of the endoluminal prosthesis of FIG. 1.

Now first looking at FIG. 1, an introducer 100 for an embodiment of an endoluminal prosthesis 101 mounted onto the introducer 100 is shown schematically. The introducer 100 has an introducer catheter 102 extending over a guide wire catheter 104. The guide wire catheter 104 extends from the distal end 108 of the introducer 100 to immediately distal of the nose cone dilator 112, which is at the proximal end 110 of the introducer 100. A sheath 116 operated by a sheath manipulator 117 is mounted on the introducer catheter 102. The sheath 116, as illustrated, is withdrawn so that the endoluminal prosthesis 101 is in an expanded position to show detail of the prosthesis 101. The sheath 116 is configured to extend over the endoluminal prosthesis 101 to the nose cone dilator 112 and keeps the endoluminal prosthesis 101 in a compressed configuration prior to deployment within the target vessel. The endoluminal prosthesis 101 is retained at its proximal end 121 by a proximal retention arrangement positioned immediately distal of the nose cone dilator 112. As shown by FIG. 2, the proximal retention arrangement may comprise loops 202 of fiber or suture material engaged with a trigger wire 204 extending from an aperture in the guide wire catheter 104 distal to the nose cone dilator 112. The loops 202 are placed so that there is formed a smaller 206 and larger 208 fold of the endoluminal prosthesis assembly 101 at its proximal end.

Figure 3:
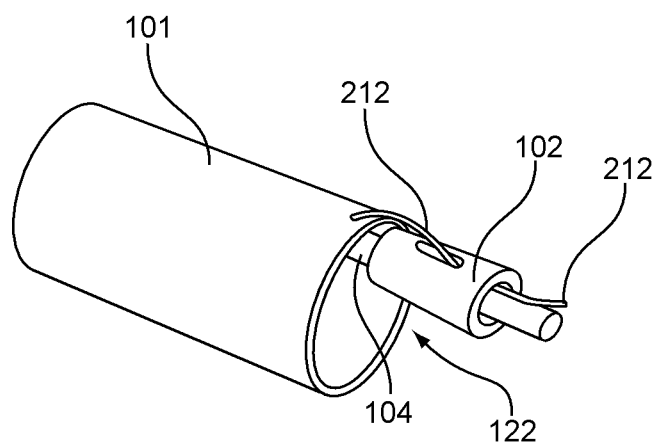
FIG. 3 shows a retention apparatus for retaining the distal end of the endoluminal prosthesis assembly of FIG. 1.

The endoluminal prosthesis 101 is retained at its distal end by another retention arrangement positioned on the introducer. As shown in FIG. 3, the distal end 122 of the endoluminal prosthesis 101 is retained on the guide wire catheter 104 just proximal of the proximal end of the introducer catheter 102 by means of a loop of trigger wire 212 extending from the introducer catheter 102. Removal of the trigger wire 212 will release the distal end 122 of the endoluminal prosthesis 101.

Referring back to FIG. 1, a handle 118 at the distal end of the introducer catheter 102 enables manipulation of the introducer 100. An indwelling catheter 120 enters a lumen (not shown) of the introducer catheter 102 at the handle 118 and exits from the introducer catheter 102 at the distal end 122 of the endoluminal prosthesis 101. Within the indwelling catheter 120, there is a guide wire 128. This guide wire 128 can be pushed through the indwelling catheter 120 so that it extends beyond the tip 130 of the nose cone dilator 112. Preferably, the proximal end of the indwelling catheter 120 is tapered to closely fit around the guide wire 128 to prevent blood loss through the indwelling catheter 120. The indwelling catheter 120 enters the lumen of the branch 124 through its distal end 125 and exits the endoluminal prosthesis assembly 101 adjacent to the nose cone dilator 112 and extends along the side of the nose cone dilator 112 in a groove 126 formed in the nose cone dilator 112.

Figure 4:
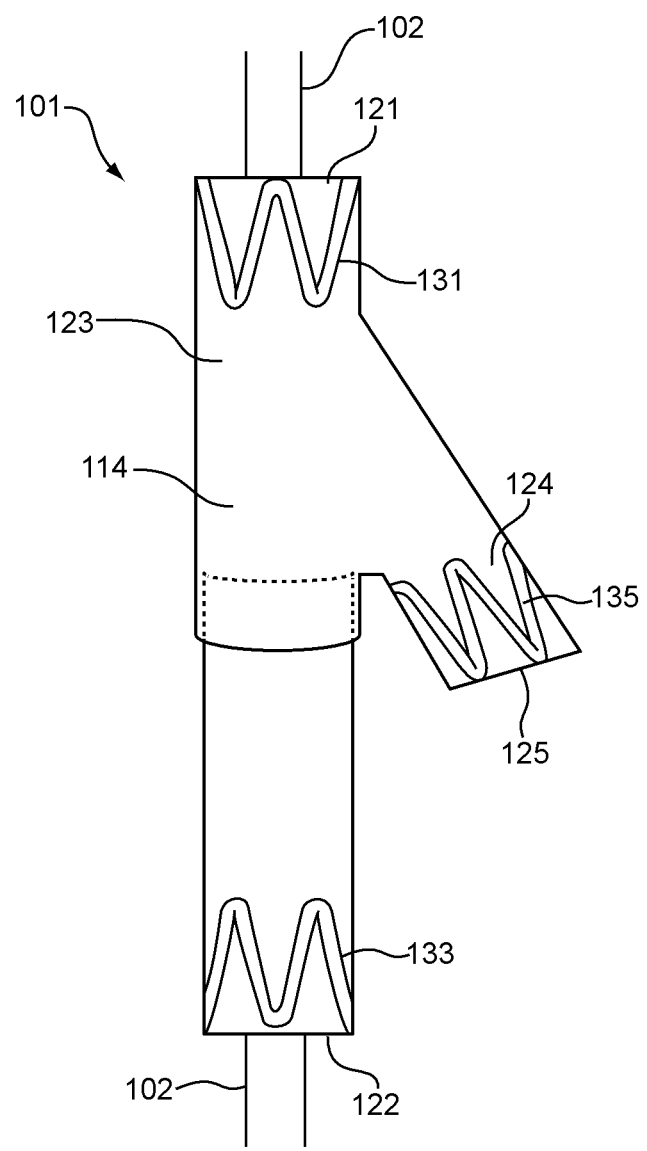
FIG. 4 shows a schematic view of the exterior of an endoluminal prosthesis assembly of FIG. 1.
Figure 5:
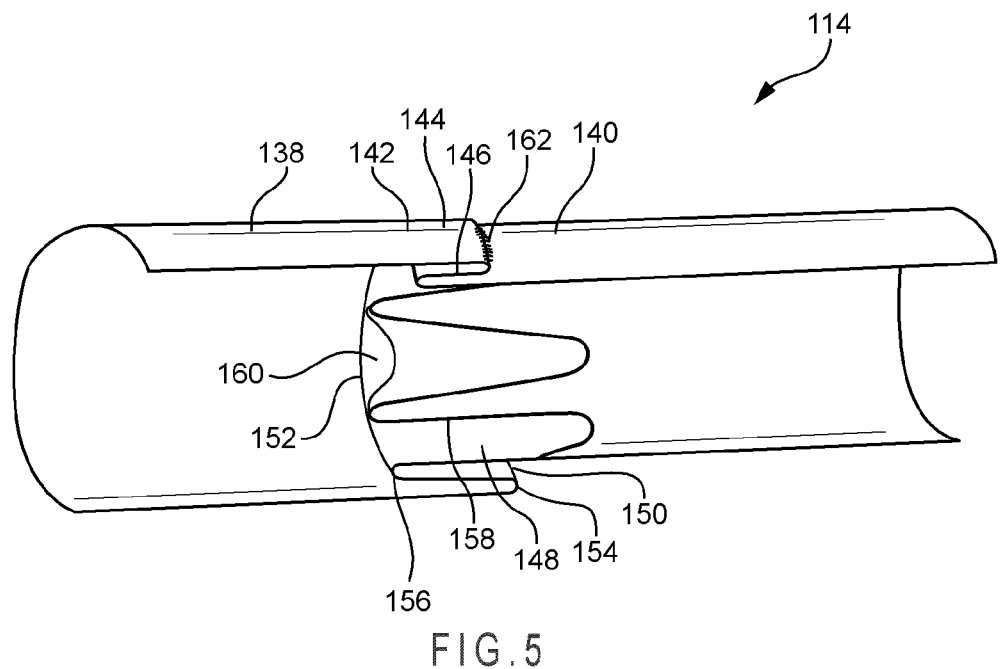
FIG. 5 shows a cross-sectional view of the endoluminal prosthesis of FIG. 1, where the endoluminal prosthesis includes a valve arrangement.

FIGS. 4 and 5 provide a more detailed view of the endoluminal prosthesis 101. Referring to FIG. 4, the endovascular prosthesis 101 includes a stent graft 114 having a substantially tubular main body 123 with a main lumen disposed therethrough and a side lumen through a branch 124. Sealing stents 131, 133 are positioned on the proximal 121 and distal ends 122, respectively, of the main body 123 of the stent graft 114. A sealing stent 135 is positioned on the distal end 125 of the branch 124 of the stent graft 114. The introducer catheter 102 is disposed through the main lumen of the stent graft 114.

The stents 131, 133, 135 may be made from numerous metals and alloys. In one example, the stents 131, 133, 135 comprise a shape-memory material such as a nickel-titanium alloy ("Nitinol"). Moreover, the structure of the stents 131, 133, 135 may be formed in a variety of ways to provide a suitable support structure. For example, one or more stents may be made from a woven wire structure, a laser-cut cannula, individual interconnected rings, or another pattern or design. While one exemplary arrangement is shown in FIG. 4, it will be appreciated that the exact number of stents, and their location, may be varied.

In one example, shown in FIG. 4, the stents 131, 133, 135 may be configured in the form of one or more "Z-stents", each of which may comprise a series of substantially straight segments interconnected by a series of bent segments. The bent segments may comprise acute bends or apices. The Z-stents are arranged in a zigzag configuration in which the straight segments are set at angles relative to each other and are connected by a bent segment. However, as noted above, the stents 131, 133, 135 may comprise any suitable configuration and one or more stents may be provided.

The stent graft 114 may be constructed from a biocompatible material. Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. For example, the stent graft 114 may be constructed from woven multifilament polyester, for example and without limitation, Dacron™, produced by DuPont. Dacron™ is known to be sufficiently biologically inert, non-biodegradable, and durable to permit safe insertion inside the human body.

FIG. 5 shows an interior view of an embodiment of the stent graft 114. The stent graft 114 includes a straight tubular proximal section 138, a straight tubular distal section 140, and a folded tubular section 142 positioned between the proximal section and the tubular section. The folded tubular section 142 is formed by folding the stent graft 114 upon itself to form three separate walls: a folded tubular section outer wall 144, a folded tubular section center wall 146, and a folded tubular section inner wall 148. The folded tubular section 142 may be positioned between adjacent circumferential rows of stents on the body 123 of the stent graft 114. In this embodiment, the folded tubular section 142 has a first circumferential fold line 150 directed toward the distal end 122 of the stent graft 114 and engaged with the proximal tubular section 138, and a second circumferential fold line 152 directed towards the proximal end 121 of the stent graft 114 and engaged with the distal section 140, which form a first end 154 and a second end 156, respectively, of the folded tubular section 142. In other embodiments, the folded tubular section 142 may comprise additional linear and nonlinear folded configurations including, but not limited to, longitudinal, angular, and helical. The straight tubular proximal section 138 is joined contiguously to the folded tubular section 142 at the first end 154, and the distal tubular section 144 is contiguously joined to the folded tubular section 142 at the second end 156. A stent 158 may be positioned within the inner wall 148 of the folded tubular section 142. The folded tubular section 142 also includes a valve arrangement 160. The valve arrangement 160 in this embodiment comprises a slit valve, which may be created by an incision in the second fold line 152 of the second end 156 of the folded tubular section 142. In other embodiments, the valve arrangement 160 may be positioned on the first fold line 150 of the first end 154. Sutures 162 may be placed about the circumference of the stent graft 114 in areas surrounding the position of the valve arrangement 160 to join a portion of the first end 154 of the folded tubular section 142 to the outer surface of the distal tubular section 140 of the stent graft 114 to maintain the folded portion, while providing sufficient access to the valve arrangement 160. Sutures may also be placed within the interior of lumen of the stent graft 114 to join a portion of the second end 156 of the folded tubular section 142 to the inner surface of the proximal tubular section 138.

The valve arrangement 160 allows one to introduce other endoluminal devices into the lumen of the stent graft 114. Once positioned through the valve arrangement 160, the endoluminal devices may access vessels through the lumen of the branch of the stent graft 114. The open diameter of the valve arrangement 160 may be sized based upon the endoluminal device that will be deployed through the valve arrangement. Particularly, the open diameter of the valve arrangement 160 may range from about 1 mm to about 4 mm. More particularly, the open diameter of the valve arrangement 160 is about 4 mm. In this embodiment, the valve arrangement 160 is positioned between adjacent apices of the stent 158. This positioning provides the operator with an improved access, which allows for an improved means of introduction of endoluminal devices into blind vessels through the interior of the stent graft 114. Radiopaque markers (not shown) may be positioned about the periphery of the valve arrangement 160 to provide a visual marker for the operator. These markers can be radiopaque material such as gold, platinum, tungsten, and any other high density material such as bands or wires.

Figure 6:
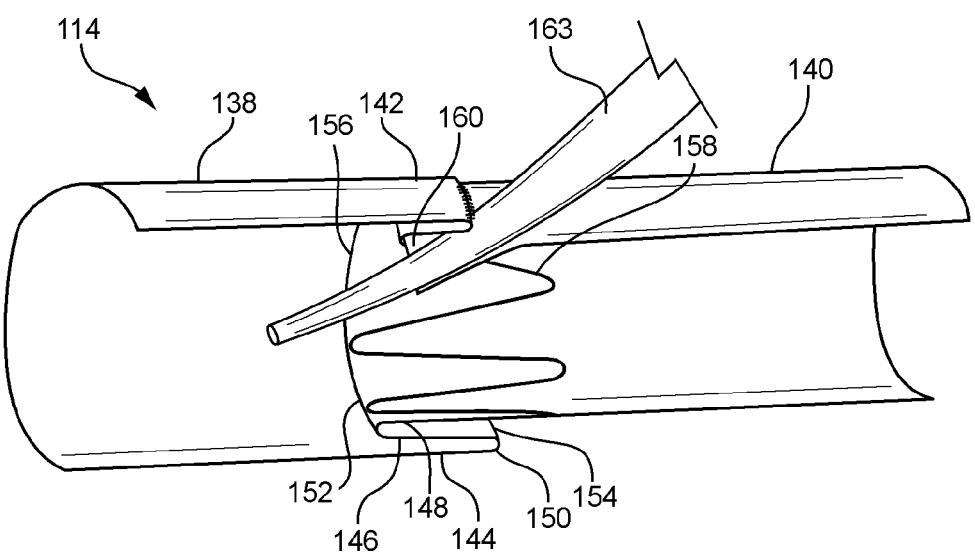
FIG. 6 shows a cross-sectional view of the endoluminal prosthesis of FIG. 1, where a catheter is introduced through the valve arrangement.

FIG. 6 discloses a cross-sectional view of the endoluminal device 101 where a second endoluminal device, such as a catheter 163, is introduced through the valve arrangement 160. The catheter 163 enters into the lumen of the stent graft 114 from the exterior through the valve arrangement 160, which forces a separation between the inner and central walls 148, 146 of the folded tubular section 142. While the catheter 163, or other endoluminal device, is deployed, the valve arrangement 160 will remain in an open position.

Figure 7:
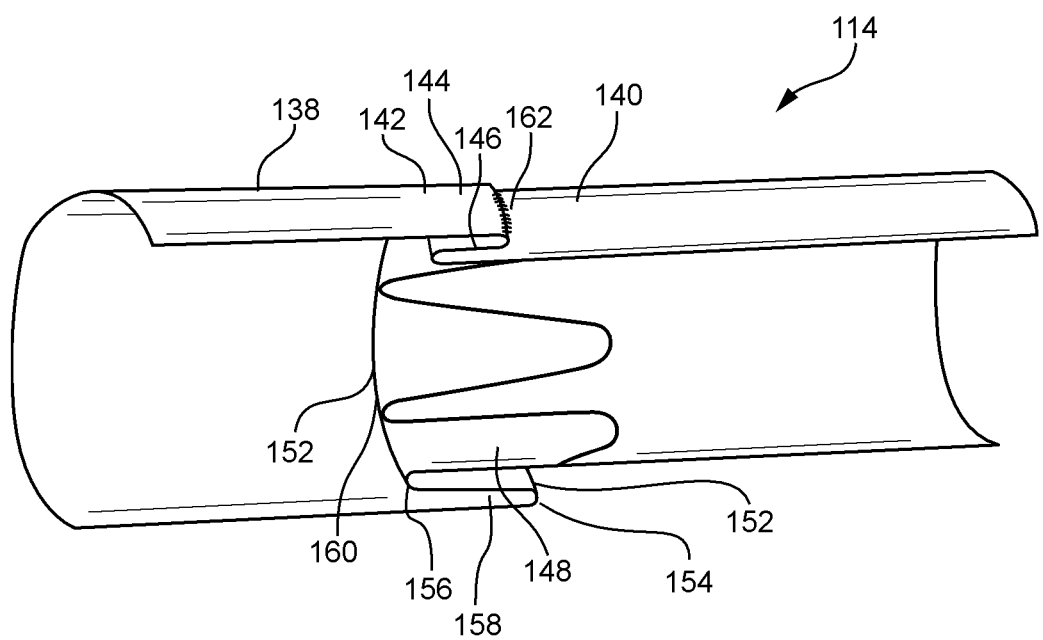
FIG. 7 shows a cross-sectional view of the endoluminal prosthesis when the valve arrangement is in a closed position.

FIG. 7 discloses a cross-sectional view of the stent graft 114 where the valve arrangement 160 is in a closed position. In the closed position, the inner wall 148 of the folded tubular section 142 engages the central wall 146 at the second end 156 and effectively seals the valve arrangement 160. The valve arrangement 160 is sealed by the pressure of the blood flowing through the lumen of the stent graft 114, as well as by the restoring axial force of the stent 158. The sealing of the valve arrangement 160 precludes the possibility of leaks out of the prosthesis 101.

In use, the operator deploys a guide wire for the introducer 100 into the femoral artery, via an incision and extended up beyond the aortic bifurcation to the aorta. The introducer 100 is deployed over the guide wire and the introducer 100 is extended up into the aortic bifurcation. The sheath 116 is withdrawn such that the stent graft 114, including the branch 124, is exposed, but retaining the stent graft 114 at both the proximal and distal ends 121, 122 so that the stent graft 114 is not in a fully expanded configuration. The operator introduces a catheter 163 into the stent graft 114 through the valve arrangement 160. Through the catheter 163, the operator can introduce additional endoluminal devices, including, but not limited to, a branch stent graft, into an internal artery through the lumen 125 of the branch 124 of the stent graft 114. Following deployment of the additional endoluminal prostheses through the valve arrangement 160, the catheter 163 is removed. Upon removal of the catheter 163 from the valve arrangement 160, the valve arrangement 160 is sealed by the restoring axial force of the stent 158 and the pressure of the blood flow through the lumen of the stent graft 114. The operator then releases the proximal 121 and distal 122 ends of the stent graft 114 by releasing trigger wires 204 and 212, respectively, and the introducer 100 is removed from the patient.

Figure 8:
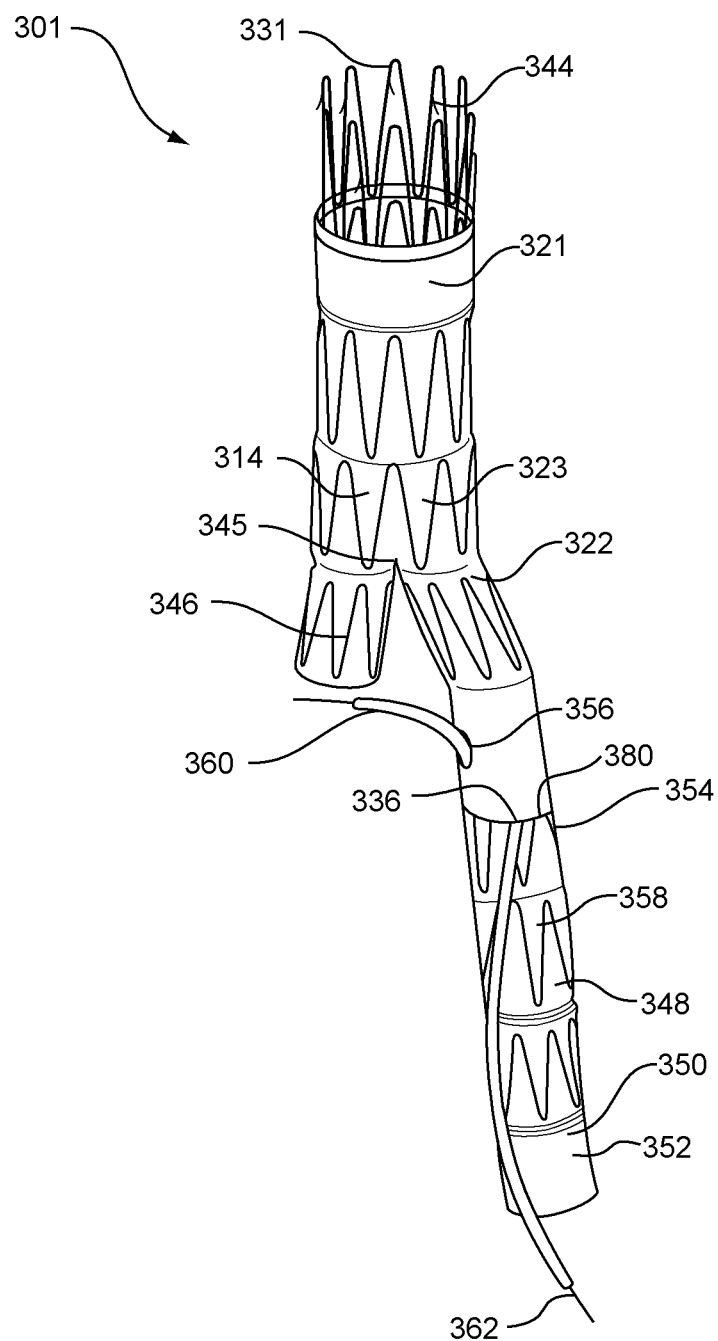
FIG. 8 shows a schematic view of an alternative embodiment of an endoluminal prosthesis.
Figure 9:
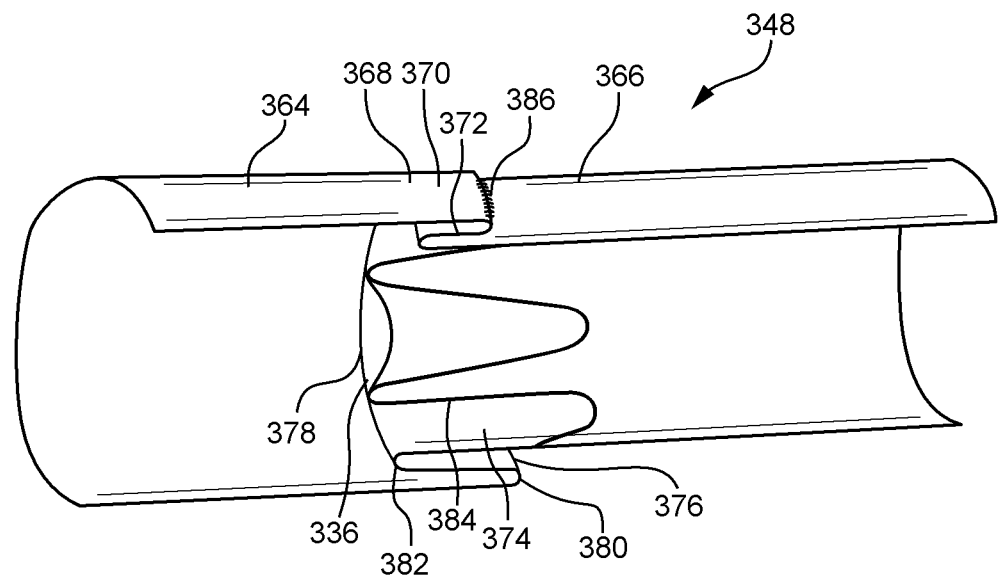
FIG. 9 shows a cross-sectional view of a portion of the longer leg of the endoluminal prosthesis of FIG. 8, where the endoluminal prosthesis includes a valve arrangement.

FIG. 8 provides an alternative embodiment of an endoluminal prosthesis assembly for the treatment of an aortic aneurysm. In this embodiment, the endoluminal prosthesis assembly 301 includes a stent graft 314. The stent graft 314 has a main body 323 having a proximal end 321 and a distal end 322 having a bifurcation 345. The stent graft 314 includes a proximally extending suprarenal stent 331 on its proximal end 321. The suprarenal stent 331 includes barbs 344 configured to engage the wall of the aorta positioned proximal of the renal arteries to secure the stent graft 314 when placed within the aorta and prevent migration within the vessel. The stent graft 314 includes a short leg 346 and a long leg 348 extending from the bifurcation 345 of the stent graft 314. The long leg 348 has a sealing surface 350 at its distal end 352. The long leg 348 also includes a fenestration 356 disposed through a side wall of the prosthesis 301. As shown in FIG. 9, the long leg 348 may include a straight tubular proximal section 364, a straight tubular distal section 366, and a folded tubular section 368 positioned between the proximal section 364 and the folded tubular section 366. During deployment of the stent graft 314 into the vasculature of a patient, an in-dwelling catheter 360 extends through the valve arrangement 336 and out through the fenestration 356. The indwelling catheter 360 includes a guide wire 362.

Figure 10:
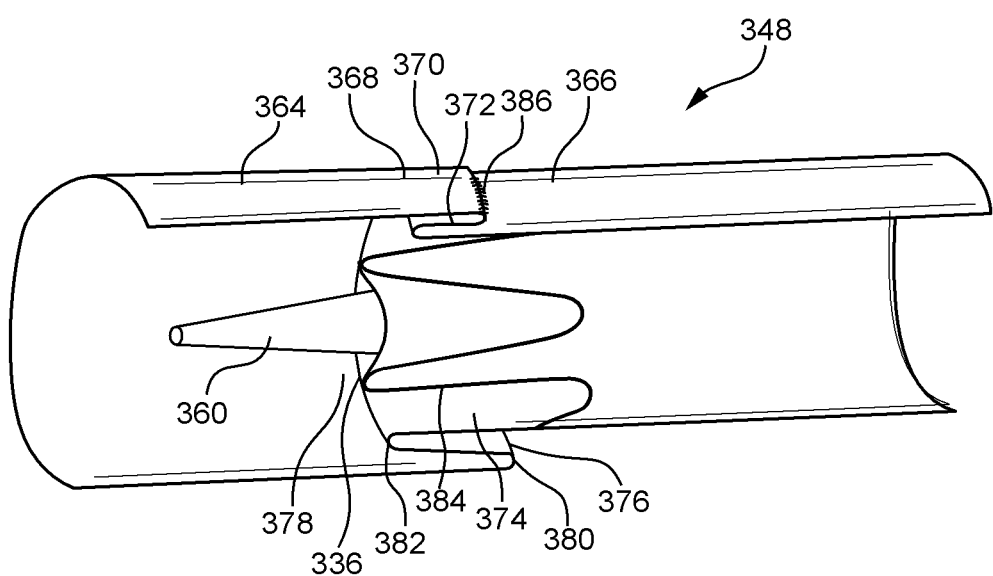
FIG. 10 shows a cross-sectional view of a portion of the longer leg of the endoluminal prosthesis of FIG. 8, where a catheter is introduced through the valve arrangement.
Figure 11:
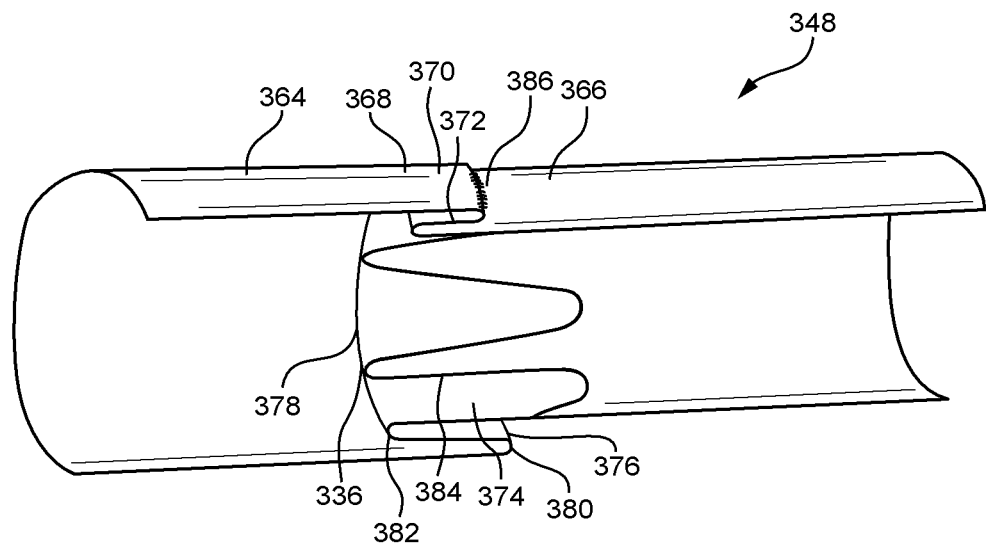
FIG. 11 shows a schematic view of the interior of the endoluminal prosthesis of FIG. 8 when the valve arrangement is in a closed position.

FIGS. 9-11 provide more detailed views of a portion of an embodiment of the long leg 348 of the stent graft 314. Referring to FIG. 9, the long leg 348 includes a straight tubular proximal section 364, a straight tubular distal section 366, and a folded tubular section 368 positioned between the proximal section and the tubular section. The folded tubular section 368 is formed by folding the long leg 348 upon itself to form three separate walls: a folded tubular section outer wall 370, a folded tubular section center wall 372, and a folded tubular section inner wall 374. The folded tubular section 368 may be positioned between adjacent circumferential rows of stents on the long leg 348. The folded tubular section 368 has a first circumferential fold line 376 directed toward the distal end of the long leg 348 and engaged with the proximal tubular section 366 and a second circumferential fold line 378 directed towards the proximal end of the long leg 348 and engaged with the distal tubular section 366, which form a first end 380 and a second end 382, respectively, of the folded tubular section 368. In other embodiments, the folded tubular section 368 may comprise additional linear and nonlinear folded configurations including, but not limited to, longitudinal, angular, and helical. The straight tubular proximal section 364 is joined contiguously to the folded tubular section 368 at the first end 380, and the distal tubular section 366 is contiguously joined to the folded tubular section 368 at the second end 382. A stent 384 may be positioned within the inner wall 374 of the folded tubular section 368. The folded tubular section 368 also includes the valve arrangement 336. The valve arrangement 336 in this embodiment comprises a slit valve, which may be created by an incision in the second fold line 378 of the second end 382 of the folded tubular section 368. In other embodiments, the valve arrangement 336 may be positioned on the first fold line 376 of the first end 380. Sutures 386 may be placed about the circumference of the long leg 348 in areas surrounding the valve arrangement 336 to join a portion of the first end 380 of the folded tubular section 368 to the outer surface of the distal tubular section 366 of the stent graft 314 to make the graft continuous, while providing sufficient access to the valve arrangement 336. Sutures may also be placed within the interior of lumen of the long leg 348 to join a portion of the second end 382 of the folded tubular section 368 to the inner surface of the proximal tubular section 364.

The valve arrangement 336 allows one to introduce other endoluminal devices into the lumen of the long leg 348. Once positioned through the valve arrangement 336, the endoluminal devices may access internal vessels, such as the iliac artery, through the fenestration 356. In this embodiment, the valve arrangement 336 is positioned between adjacent apices of the stent 384, which provides adequate space for an operator to introduce additional endoluminal devices.

FIG. 10 discloses a cross-sectional view of the endoluminal device 301 where a second endoluminal device, such as an indwelling catheter 360, is introduced through the valve arrangement 336. The catheter 360 enters into the lumen of the stent graft 314 from the exterior through the valve arrangement 336, which forces a separation between the inner 374 and central walls of the folded tubular section 372. While the catheter 360, or other endoluminal device, is deployed, the valve arrangement 336 will remain in an open position.

FIG. 11 discloses an embodiment of the long leg 348 where the valve arrangement 336 is in a closed position. In the closed position, the inner wall 374 of the folded tubular section 368 engages the central wall 372 along the second fold line 378 second end 382 and effectively seals the valve arrangement 336. The valve arrangement 336 is sealed by the pressure of the blood flowing through the lumen of the long leg 348, as well as by the restoring force of the stent 384. The sealing of the valve arrangement 336 prevents the possibility of leaks out of the prosthesis.

In use, a guide wire for an introducer is inserted into the femoral artery, via an incision and extended up beyond the aortic bifurcation to the aorta. The operator deploys the introducer over the guide wire and it is positioned within the aorta of a patient. The main body 323, the short leg 346 and the long leg 348 of the stent graft 314 are deployed, while retaining the superenal stent 331 on the proximal end 321 of the stent graft 314. The operator introduces a catheter 360 into the long leg 348 through the valve arrangement 336 and into the lumen of the long leg 348. Through the catheter 360, the operator can introduce additional endoluminal devices, including, but not limited to, a branch stent graft, into an internal artery through the fenestration 356. Following deployment of the additional endoluminal prostheses through the valve arrangement 336, the catheter 360 is removed. Upon removal of the catheter 360 from the valve arrangement 336, the valve arrangement 336 is sealed by the restoring axial force of the stent 384 and the pulsating flow of the blood through the lumen of the long leg 348. The valve arrangement 336 is sealed by the restoring force of the stent 384 and the pressure of the blood flow through the lumen. The operator then releases the suprarenal stent 331 on the second end 321 of the stent graft 314, and the delivery device is removed from the patient.

Figure 12A:
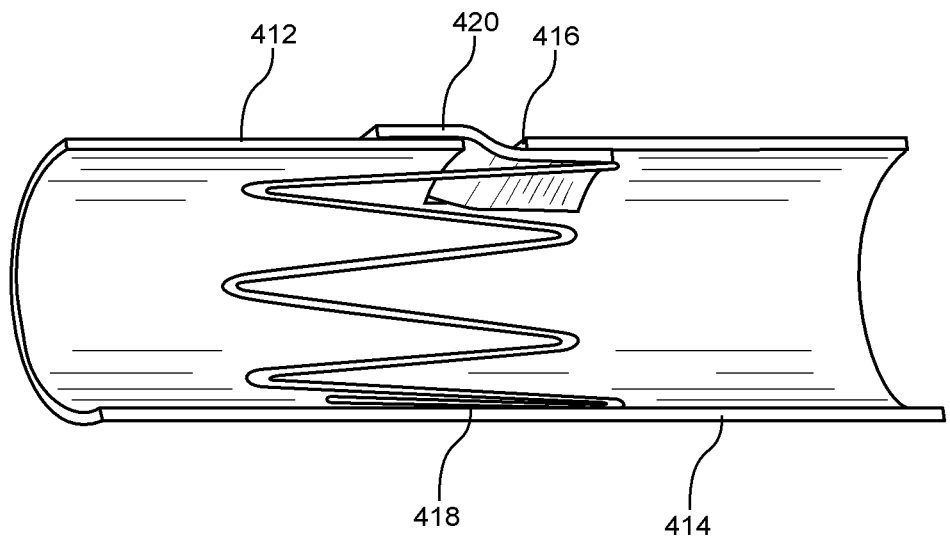
FIGS. 12a and 12b show an alternative embodiment of an endoluminal prosthesis.
Figure 12B:
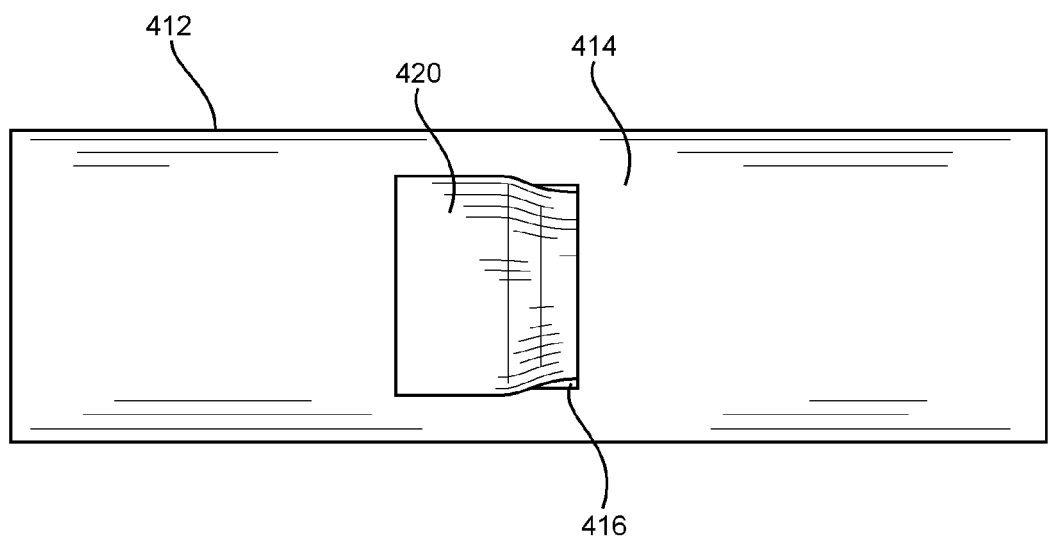

FIGS. 12a and 12b show a portion of an alternative embodiment of the valve of an endoluminal prosthesis assembly for the treatment of an aortic aneurysm. Referring to FIG. 12a, the endoluminal prosthesis 412 includes a stent graft 414 that is a substantially tubular body and has a main lumen disposed therethrough. The stent graft 414 includes a valve arrangement 416. The valve arrangement 416 in this embodiment comprises a slit valve, which may be created by an incision in the body of the stent graft. As shown, the slit valve is positioned in circumferentially about a section of the outer surface of the stent graft. In other embodiments, the slit valve may have a different configuration, such as, but not limited to, longitudinal. The open diameter of the valve arrangement 416 may be sized based upon the endoluminal device that will be deployed through the valve arrangement. Particularly, the open diameter of the valve arrangement 416 may range from about 1 mm to about 4 mm. More particularly, the open diameter of the valve arrangement 416 is about 4 mm. The valve arrangement 416 is generally held in a closed position through the use of a stent 418. The stent 418 may be positioned within the inner surface of the stent graft 414 distal to the slit valve. The stent 418 may be configured in the form of a "Z-stents", which may comprise a series of substantially straight segments interconnected by a series of bent segments. The bent segments may comprise acute bends or apices. However, the stent 418 may comprise any suitable configuration and one or more stents may be provided. In the embodiment shown in FIG. 12a, the stent 418 is disposed completely about the circumference of the inner surface of the stent graft 414. In alternative embodiments, the stent 418 may be positioned only partially around the circumference of the stent graft 414.

A piece of graft material 420 may be positioned through the valve arrangement 416 to help seal the slit valve when it is not in use. The graft material 420 is biocompatible and may be the same material used to construct the stent graft 414. In other embodiments, the graft material 420 may comprise material having at least one characteristic different than that material used to construct the stent graft 414. As shown in FIG. 12a, a portion of the graft material 420 is positioned within the main lumen of the stent graft 414. In this embodiment, the graft material 420 is secured to the inner surface of the stent graft 414 through the use of the stent 418. In alternative embodiments, the graft material 420 may be secured using other means and methods, including, but not limited to, adhesives and sutures. As shown in FIG. 12b, a portion of the graft material 420 is positioned on the outer surface of the stent graft 414. This portion of the graft material 420 may be secured to the outer surface of the graft material through methods including, but not limited to, adhesives and sutures.

Throughout this specification various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, that are intended to define the spirit and scope of this invention.

The invention claimed is:

1. An endoluminal prosthesis comprising:
   a graft having a tubular configuration defining a lumen therethrough, the graft having a proximal end, a distal end, a proximal section and a distal section;
   a folded section positioned between the proximal section and the distal section, the folded section having a first fold directed toward the distal end and engaged with the proximal section and a second fold directed toward the proximal end and engaged with the distal section; and
   a valve arrangement positioned in at least one of the first and second folds.

2. The endoluminal prosthesis of claim 1, where the second fold of the folded section is at least partially disposed within the lumen of the graft.

3. The endoluminal prosthesis of claim 1, where the proximal section is contiguous with the first fold of the folded section and the distal section is contiguous with the second fold of the folded section.

4. The endoluminal prosthesis of claim 1, where the folded section further includes an inner wall, a central wall, and an outer wall formed from the first and second folds.

5. The endoluminal prosthesis of claim 4, where the outer wall of the folded section is joined to the distal section about an outer surface of the graft by sutures.

6. The endoluminal prosthesis of claim 1, where the valve arrangement is disposed through the second fold of the folded section.

7. The endoluminal prosthesis of claim 1, where the valve arrangement comprises a slit valve.

8. The endoluminal prosthesis of claim 1, where the valve arrangement is positioned between two adjacent apices of a stent attached to an exterior surface of the graft.

9. An endoluminal prosthesis assembly comprising:
   a graft comprising a main graft body having a tubular configuration defining a lumen therethrough;
   at least one leg section attached distal to the main graft body and having a lumen in fluid communication with the main lumen; the leg section having a proximal section and a distal section;
   a folded section positioned between the proximal section and the distal section of the leg section, the folded section having a first fold directed toward the distal end and engaged with the proximal section and a second fold directed toward the proximal end and engaged with the distal section; and
   a valve arrangement positioned in at least one of the first and second folds.

10. The endoluminal prosthesis assembly of claim 9, where the second fold of the folded section is partially disposed within the lumen of the graft.

11. The endoluminal prosthesis of claim 9, where the folded section further includes an inner wall, a central wall, and an outer wall formed from the first and second folds.

12. The endoluminal prosthesis of claim 11, where the outer wall of the folded section is joined to an outer wall of the distal section about an exterior surface of the graft by sutures.

13. The endoluminal prosthesis of claim 9, where the valve arrangement is disposed through the second fold of the folded section.

14. The endoluminal prosthesis of claim 9, where the valve arrangement is positioned between two adjacent apices of a stent attached to an exterior surface of the graft.

15. An endoluminal prosthesis comprising:
   a graft having a tubular configuration defining a lumen therethrough, the graft having a proximal section and a distal section;
   a plurality of stents attached about an outer surface of the graft, the stents having a generally undulating configuration; a folded section positioned between the proximal section and the distal section, the folded section having a first fold directed toward the distal end and engaged with the proximal section and a second fold directed toward the proximal end and engaged with the distal section; and a slit valve arrangement disposed in at least one of the first and second folds.

16. The endoluminal prosthesis of claim 15, where the slit valve arrangement has an open diameter of about 4 mm.

17. The endoluminal prosthesis of claim 15, where the folded section further includes an inner wall, a central wall, and an outer wall formed from the first and second folds.

18. The endoluminal prosthesis of claim 17, where the outer wall of the folded section is joined to an outer wall of the distal section to form a contiguous stent graft.

19. The endoluminal prosthesis of claim 15, further comprising a stent positioned about an inner surface of the graft distal to the slit valve arrangement, the stent configured to seal the slit valve arrangement.

* * * * *